US012623189B2

(12) United States Patent
Assmann et al.

(10) Patent No.: US 12,623,189 B2
(45) Date of Patent: May 12, 2026

(54) PROCESS FOR TESTING FILTERS

(71) Applicant: GAMBRO LUNDIA AB, Lund (SE)

(72) Inventors: Claudia Assmann, Rangendingen (DE);
Ralf Flieg, Rangendingen (DE);
Wolfgang Freudemann, Hechingen
(DE); Torsten Knoer, Burladingen
(DE); Mehmet Yildirim, Hechingen
(DE)

(73) Assignee: GAMBRO LUNDIA AB, Lund (SE)

( * ) Notice: Subject to any disclaimer, the term of this patent is extended or adjusted under 35 U.S.C. 154(b) by 753 days.

(21) Appl. No.: 16/638,554

(22) PCT Filed: Aug. 15, 2018

(86) PCT No.: PCT/EP2018/072092
§ 371 (c)(1),
(2) Date: Feb. 12, 2020

(87) PCT Pub. No.: WO2019/034678
PCT Pub. Date: Feb. 21, 2019

(65) Prior Publication Data
US 2020/0215493 A1 Jul. 9, 2020

(30) Foreign Application Priority Data
Aug. 16, 2017 (EP) ..................................... 17186479

(51) Int. Cl.
B01D 65/10 (2006.01)
A61M 1/16 (2006.01)
(Continued)

(52) U.S. Cl.
CPC ............. B01D 65/102 (2013.01); A61M 1/16 (2013.01); B01D 61/243 (2013.01); B01D 69/08 (2013.01);
(Continued)

(58) Field of Classification Search
CPC ......... G01N 15/0826; G01N 2015/084; A61M 2205/705; A61M 1/16; B01D 65/102; B01D 61/243; B01D 69/08
See application file for complete search history.

(56) References Cited

U.S. PATENT DOCUMENTS 5,808,181 A 9/1998 Wamsledler et al.
5,900,270 A * 5/1999 Smith, III ............ B01D 65/102
427/230

(Continued)

FOREIGN PATENT DOCUMENTS

EP 0958852 11/1999
EP 1775015 4/2007
EP 1897605 3/2008

OTHER PUBLICATIONS

PCT Search Report and Written Opinion prepared for PCT/EP2018/072092, completed Oct. 8, 2018.

*Primary Examiner* — Benjamin L Lebron
*Assistant Examiner* — Bernadette Karen McGann
(74) *Attorney, Agent, or Firm* — Barnes & Thornburg LLP

(57) ABSTRACT
The present disclosure relates to a process for testing the integrity of membranes in a filter module. Specifically, the process is applied to filters for extracorporeal blood treatment, in particular, filters comprising both filter membranes and particulate material.

19 Claims, 3 Drawing Sheets

(51) Int. Cl.
 _B01D 61/24_ (2006.01)
 _B01D 69/08_ (2006.01)
 _G01N 15/08_ (2006.01)
(52) U.S. Cl.
 CPC ... _G01N 15/0826_ (2013.01); _A61M 2205/705_
 (2013.01); _G01N 2015/084_ (2013.01)

(56) References Cited

U.S. PATENT DOCUMENTS

| | | | | |
|---|---|---|---|---|
| 6,065,329 A * | 5/2000 | Fukada | ................ | B01D 65/102 |
| | | | | 73/40 |
| 2005/0229681 A1 | 10/2005 | Yamaguchi et al. | | |
| 2007/0089489 A1* | 4/2007 | Lewnard | ............. | B01D 65/102 |
| | | | | 73/40 |
| 2013/0205873 A1* | 8/2013 | Wagner | ................ | G01N 15/082 |
| | | | | 73/38 |
| 2015/0290380 A1* | 10/2015 | Welzel | ................ | A61M 1/3472 |
| | | | | 210/638 |

* cited by examiner

PROCESS FOR TESTING FILTERS

CROSS-REFERENCE TO RELATED APPLICATIONS

This application is the U.S. national phase of PCT/EP2018/072092, filed on Aug. 15, 2018, which claims the benefit of European Patent Application Serial Number 17186479.6, filed on Aug. 16, 2017, the entire disclosures of both of which are incorporated herein by reference.

TECHNICAL FIELD

The present disclosure relates to a process for testing the integrity of membranes in a filter module. Specifically, the process is applied to filters for extracorporeal blood treatment, in particular, filters comprising both filter membranes and particulate material.

DESCRIPTION OF THE RELATED ART

Diffusion and/or filtration devices comprising hollow fiber membranes are used in various medical treatments which remove unwanted substances from body fluids, e.g., blood. Examples of such treatments are hemodialysis, hemodiafiltration and hemofiltration. Membrane filters are also used in the production of sterile liquids, by causing the liquid to pass through a semi-permeable membrane able to filter the germs. Various processes for checking the integrity of a filter have been described.

One of the known processes is the bubble point test (BPT), which can check on the absence of membrane pores having pores which have a greater size than a predetermined limit. The BPT considers the membrane pores as capillary tubes, and the maximum radius of the pores is determined by pressure measurements. The test briefly comprises the following stages: the membrane is wetted so that the pores are full of liquid; a first side of the membrane is connected to a gas source, while the opposite side is connected to a liquid for easy detection of gas bubbles; the first side of the membrane is gradually pressurized with the gas; while the gas pressure on the first side remains relatively low, a modest amount of gas will displace, by diffusion, through the liquid contained in the membrane pores towards the second side of the membrane; this amount of gas flow is proportional to the speed of increase of gas pressure on the first side; when the gas pressure reaches a certain level, the liquid contained in the largest pores is forced to exit from the pores themselves, and a considerable amount of gas crosses the largest pores, reaching the liquid connected to the second side of the membrane, forming gas bubbles within the liquid; in this situation a further pressuring action leads to a further displacement of gas towards the second side of the membrane, with no discernible increase in pressure; the substantially stable pressure reached in this situation (bubble point pressure, or BP pressure) is a known function of the maximum radius of the membrane pores and thus enables determination thereof; stopping the pressurization action leads to a situation of substantial equilibrium in the BP pressure.

U.S. Pat. No. 5,064,529 A describes an automatic BPT (without the need to observe the moment of gas bubble formation) to check whether the effective BP pressure of the membrane corresponds to the desired BP pressure corresponding to the maximum diameter of the pores indicated by the membrane manufacturer; in a first stage the first side of the membrane is pressurized with the gas at a predetermined constant pressurization speed, at the end of which first stage the pressure measured on the first side of the membrane should correspond to a predetermined theoretical pressure; the pressurization speed and the pressurization time are chosen so that the above-mentioned theoretical pressure is lower than the desired BP pressure; if the pressure measured after the predetermined time does not correspond to the theoretical pressure, a fault is signaled due, probably, to the breakage of the membrane or a faulty installation of the filter; in a second stage, the pressurization is halted for a certain time period in which the pressure should remain substantially constant; if, on the contrary, there is a significant drop in pressure, a fault is signaled due, probably, to the faulty filling-up of the pores with the liquid; in a third stage, the pressurization of the first side of the membrane is re-established at a predetermined speed for a predetermined time, during which theoretically the desired BP pressure is reached; if, at the end of the third stage, the desired BP pressure is measured, within a predetermined range of acceptability, it is considered that the maximum diameter of the pores is the desired one.

U.S. Pat. No. 5,594,161 A describes a process for testing the integrity of one or more filtering elements in which the inlet side of the filter element is wetted and subjected to a gas pressure which is kept constant, while the pressure is measured on the outlet side which, previously, has been made part of a closed system. If, after a predetermined time, the outlet pressure does not exceed a predetermined threshold value, the filter element is considered intact.

U.S. Pat. No. 4,614,109 A describes a process for checking the permeability of a wet membrane of a filter, based both on a search for the BP pressure and on the determination of the gas diffusion before reaching BP pressure. In this process, the filter membrane is first impregnated with liquid; thereafter, the inlet side of the membrane is gradually pressurized by introduction of a gas; the gas that passes by diffusion through the membrane is collected in a graduated container; the permeability of the membrane is calculated on the basis of the transmembrane pressure measured on the two sides of the membrane, and of the quantity of gas diffused through the membrane per unit of time using the graduated container. By continuing with the pressurization, at a certain point (called the visual bubble point because it can be visually detected) the production of gas bubbles on the exit side of the membrane sharply increases: this, as mentioned above, is due to the fact that, on reaching the bubble point pressure, the passage of gas through the membrane occurs both by diffusion (in a small part) and (prevalently) by effect of the formation of gas conduits through the pores of the membrane.

U.S. Pat. No. 6,228,271 A describes a process for testing the integrity of filter membranes in which the filter inlet chamber is emptied of liquid and filled with air at atmospheric pressure, while the outlet chamber remains full of liquid. A depression is then created in the outlet chamber in order to create a transmembrane pressure; after the depression has been stabilized, for example at a value comprised between 0.2 and 0.9 bar (absolute pressure), and before completely evacuating the liquid from the outlet chamber, the constant flow of liquid is measured as it exits the outlet chamber, which corresponds to the air flow passing through the perforations of the membrane; the integrity of the membrane is thus measured on the basis of the value measured for the liquid flow.

Another known process for measuring the integrity of a filter membrane involves verification under sealed pressure, where a transmembrane pressure gradient is created and monitored over time in at least one chamber of the filter. A typical sealed pressure test involves, for example, a side of the membrane being brought up to a predetermined gas pressure, below BP pressure, comprised in the diffusion range, i.e., a range in which the pressure in the second membrane chamber increases proportionally to the pressure in the first side; when the pressure has been reached, the gas supply is interrupted and the pressure on the first side monitored; if the drop in pressure per time unit exceeds a predetermined threshold value, the membrane is understood to exhibit some defects.

U.S. Pat. No. 4,702,829 A describes a process, of the pressurized sealed type, for verifying the integrity of the filters of a hemodiafiltration apparatus, in which the substitution liquid is realized on-line by passing the dialyzer liquid through two sterile filters arranged one after another, each of which exhibits two chambers separated by a water-wettable and semi-permeable membrane, which can hold the germs. The verification process of the filter seal begins after the dialysis circuit washing stage, with the circuit full of the detergent liquid and the water-wettable filter membranes wet. The filter seal verification process uses an ultrafiltration pump, predisposed in the dialysis circuit downstream of the blood treatment device and used in the dialysis treatment for obtaining a patient weight drop measurement. During the filter test, the ultrafiltration pump is used to aspirate air internally of the first chamber of the second filter, through a micro-porous water-repelling filter arranged in a breather of the first chamber. The aspirated air can also enter the second chamber of the first filter in the absence of occlusions in the circuit branch comprised between the two filters. The liquid that leaves space for the aspirated air is removed by the ultrafiltration pump through the membranes of the two filters. Given that the water-wettable membranes of the filters are wet, the membranes themselves are substantially impermeable to air. Therefore, once the second chamber of the first filter and the first chamber of the second filter are entirely occupied by air at atmospheric pressure, and since the air that has entered the chambers cannot escape through the membrane, the ultrafiltration pump can generate a depression in chambers occupied by the liquid, i.e. the first chamber of the first filter and the second chamber of the second filter. The ultrafiltration pump is then activated until a determined depression has been reached in a part of the dialysis circuit filled with liquid. Thereafter, the depression is monitored using a pressure gauge, for example by measuring the time necessary for the pressure to rise by a predetermined quantity, or by measuring the depression after a determined period of time. The monitoring of the depression enables an evaluation of the fluid seal of the system constituted by the membranes and the part of the circuit under depression.

U.S. Pat. No. 5,808,181 A describes a process for verifying membrane filters arranged in the dialysis circuit of a device for extracorporeal blood treatment, in which the membrane of a filter to be checked is completely wetted with a liquid, a branch of the dialysis circuit containing one of the two filter chambers to be verified is separated from the rest of the circuit, a gas is injected into the separated branch to cause an overpressure, while the liquid contained in the chamber is removed by passing through the membrane; the gas supply is interrupted after a predetermined overpressure level has been reached in chamber; thereafter, the overpressure is controlled, for example by comparing the pressure drop per time unit with a limit value which is characteristic of an intact filter membrane.

EP-A 0 407 737 B1 describes a process for testing the membrane of a dialyzer filter in two stages: in a first stage the blood chamber of the dialyzer is subjected to a pressure gradient from the blood chamber to the dialyzer fluid chamber; in a second stage the membrane is subjected to an opposite gradient. The test enables a determination of the presence of leaks which might appear or be noted only by effect of one or other of the two pressure gradients.

EP-A 1 898 973 B1 discloses a process for testing filters of treatment fluid of a hemodiafiltration apparatus, wherein each filter has a wet semipermeable membrane which separates a gas-filled first chamber from a liquid-filled second chamber. The first chambers are pressurized by a pump supplying air, while the second chambers are placed in depression by a drainage pump of used dialysis fluid. A first closed system is formed which includes the first chambers and a second closed system is formed which includes the second chambers. Two pressure gauges monitor the pressure in the two closed systems for a predetermined time.

SUMMARY

A principal aim of the present invention is to provide a reliable and fast process for the testing of filters comprising two compartments separated by a porous membrane; particularly filters wherein one compartment additionally comprises particulate matter, e.g., polymer beads. The test involves the use of particular testing fluids and/or testing gases which permit to identify with higher accuracy filters with defective membranes.

DETAILED DESCRIPTION

Figure 1:
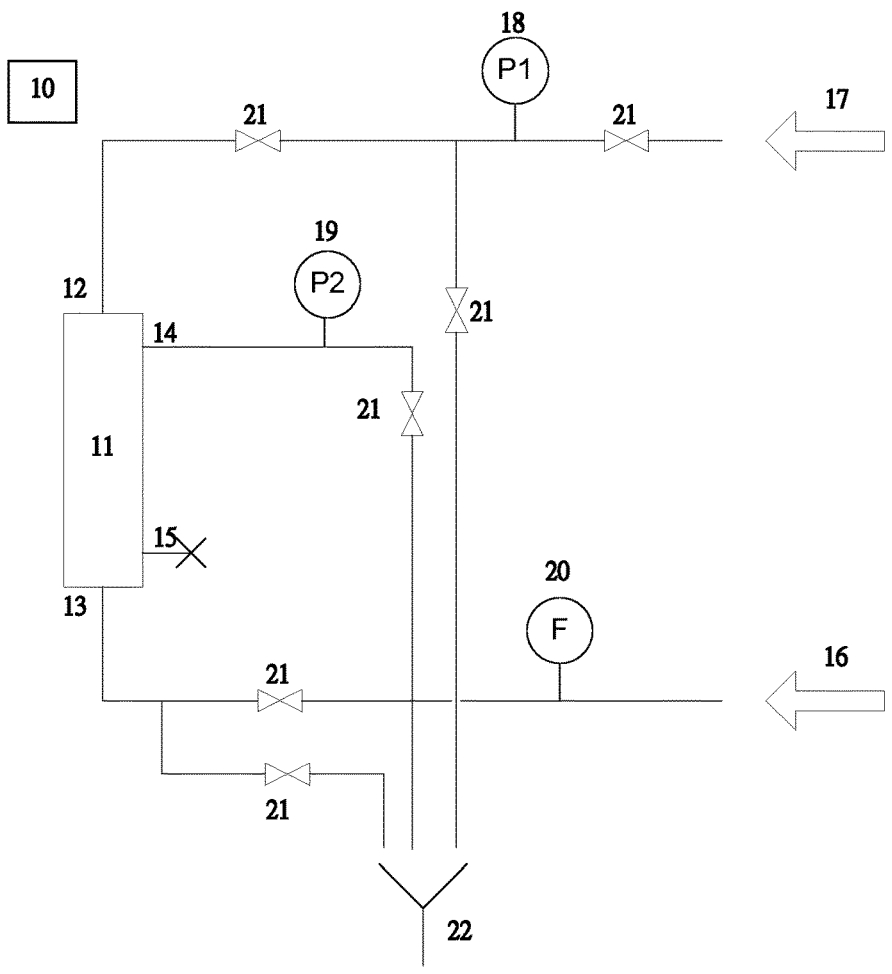
FIG. 1 shows an apparatus for testing the integrity of membranes in a filter device.

The present invention provides a process for testing a filter comprising two compartments separated by a porous membrane, comprising i) providing a filter having both compartments filled with a testing liquid;

ii) introducing a testing gas into one of the compartments, displacing the testing liquid from the compartment, and establishing a pressure gradient between the compartments;

iii) monitoring the pressure gradient between the compartments or measuring flow of the testing gas through the membrane, wherein the testing liquid is selected from the group consisting of water; aqueous solutions of physiologically acceptable salts; and aqueous solutions of polysorbates; and the testing gas is selected from the group consisting of nitrogen; air; noble gases like helium, neon, argon, krypton, and xenon; $SF_6$; and perfluorinated (cyclo)alkanes like $C_2F_6$, $C_3F_8$, and $C_4F_8$;

with the proviso that the combination of water as testing liquid and nitrogen, air, helium, neon, argon or krypton as testing gas is excluded.

The process of the present disclosure is suitable for testing the integrity of filters comprising two compartments separated by a porous membrane. Examples of such filters are membrane filters used in extracorporeal blood treatment, e.g. dialyzers; filters used in the preparation of medical fluids, e.g., pyrogen-free and germ-free fluids like dialysis fluid or substitution fluid; virus filters; blood oxygenators; and reverse osmosis filters. The process of the present disclosure is particularly useful for testing the integrity of filters wherein one compartment additionally comprises particulate matter, e.g., polymer beads or particles comprising activated carbon. Examples of filters additionally comprising particulate material have been described in EP 2 735 326 B1 and EP 2 735 360 B1, respectively.

Each one of the two compartments of the filter generally has at least one fluid inlet or outlet, respectively. In one embodiment, each of the two compartments has one fluid inlet and one fluid outlet. In another embodiment, only one of the compartments has both a fluid inlet and a fluid outlet, while the other compartment only has a fluid inlet. In still another embodiment, only one of the compartments has both a fluid inlet and a fluid outlet, while the other compartment only has a fluid outlet. In still another embodiment, only one of the compartments only has a fluid inlet, while the other compartment only has a fluid outlet. In a particular embodiment, one compartment has a fluid inlet and a fluid outlet, and the other compartment either has neither fluid inlet nor fluid outlet, or a fluid inlet and a fluid outlet of the compartment have been sealed permanently.

The porous membrane of the filter may take different forms. In one embodiment, the membrane is a flat sheet membrane or a stack of flat sheet membranes. In another embodiment, the porous membrane is a hollow fiber membrane or a bundle of hollow fiber membranes.

The porous membrane may be hydrophilic or hydrophobic, and are comprised of synthetic polymers. Examples of suitable membrane materials comprise hydrophobic polymers like polysulfones, polyethersulfones, polyacrylonitrile (PAN) and its copolymers, polytetrafluoroethylene, polyvinylidene fluoride, and hydrophilic polymers like polyvinylpyrrolidone (PVP), polyetherimine (PEI) or EVA.

The testing liquid is a liquid which is able to wet the membrane surface and fill the pores of the membrane. Suitable testing liquids are chosen according to the properties of the membrane. For hydrophilic membranes, the testing liquid is selected from the group consisting of water; and aqueous solutions of physiologically acceptable salts, or aqueous solutions of polysorbates.

Suitable aqueous solutions of polysorbates comprise 0.5 to 3 wt. % polysorbate, for instance 0.5 to 2 wt. %, e.g., 1 wt. %. Polysorbates are derived from ethoxylated sorbitan esterified with fatty acids. Common brand names for polysorbates include Scattics®, Alkest®, Canarcel®, and Tween®. Examples include Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), and Polysorbate (polyoxyethylene (20) sorbitan monooleate). The number 20 following the 'polyoxyethylene' part refers to the total number of oxyethylene —$(CH_2CH_2O)$— groups found in the molecule. The number following the 'polysorbate' part is related to the type of fatty acid associated with the polyoxyethylene sorbitan part of the molecule. Monolaurate is indicated by 20, monopalmitate is indicated by 40, monostearate by 60, and monooleate by 80. In one embodiment, an aqueous solution of Polysorbate 20 is used as testing liquid. In a further embodiment, the concentration of Polysorbate 20 in the testing liquid is 1 wt. %.

Suitable aqueous salt solutions are solutions of physiologically acceptable salts. In one embodiment, the testing liquid is an aqueous salt solution having a salt concentration in the range of from 5 wt. % to 30 wt. %, for instance, 10 to 20 wt. %. Examples of physiologically acceptable salts include chlorides, carbonates, hydrogen carbonates, sulfates, hydrogen sulfates, and carboxylates like lactates, acetates, or citrates of ammonium; alkali metals like sodium; or alkaline earth metals like magnesium or calcium. In one embodiment, the salt is sodium chloride. In another embodiment, the salt is ammonium sulfate.

The testing gas is selected from the group consisting of nitrogen; air; noble gases like helium, neon, argon, krypton, and xenon; $SF_6$; and perfluorinated (cyclo)alkanes, e.g., $C_2F_6$, $C_3F_8$, and $C_4F_8$. If water is used as the testing liquid, the testing gas is not nitrogen, air, helium, neon, argon nor krypton. In this case, the testing gas is selected from the group consisting of sulfur hexafluoride ($SF_6$) and perfluorinated (cyclo)alkanes, e.g., hexafluoroethane ($C_2F_6$), octafluoropropane ($C_3F_8$), or octafluorocyclobutane ($C_4F_8$).

At the beginning of the process of the present disclosure, a filter having both compartments filled with a testing liquid is provided.

In one embodiment starting from a dry filter, the filter is first filled with the testing liquid. In a particular embodiment, the dry filter is evacuated and connected to a reservoir of the testing liquid. The testing liquid is sucked into the filter, filling both compartments and wetting the porous membrane. In one embodiment of the process, the pressure in the filter is reduced by connecting one compartment of the filter to a vacuum line or a vacuum pump, and, subsequently or simultaneously, connecting the other compartment to a reservoir containing the testing liquid, so that the testing liquid is sucked into the filter. In another embodiment of the process, the entire filter is evacuated, all inlets/outlets of the filter are closed and one of the inlets is subsequently connected to a reservoir containing the testing liquid. In still another embodiment of the process, one compartment of the filter is connected to a pressurized reservoir containing a testing liquid, so that the pressure forces the testing liquid into the filter.

In another embodiment starting from a filter comprising a liquid which is not the desired testing liquid, for instance, a water-filled or liquid-filled filter, the filter is emptied and subsequently filled with the testing liquid. In an alternative embodiment starting from a filter comprising a liquid which is not the desired testing liquid, for instance, a water-filled or liquid-filled filter, the liquid in the filter is replaced with the testing liquid, for instance, by flushing the filter with the testing liquid, thereby displacing the liquid initially present in the filter.

In one embodiment, the filter having both compartments filled with a testing liquid is degassed before a testing gas is introduced. Residual air is removed from the filter to make sure that the pores of the membrane are completely filled with the testing liquid, that the testing liquid does not contain any dissolved gas that could impair the measurements, and that air is removed even from spaces within the device which are difficult to access, i.e., dead zones.

The pores of the membrane are filled with the testing liquid. As a result, gas permeability of the membrane is substantially reduced and the membrane becomes largely impermeable to gas, if the membrane is intact.

A testing gas is introduced into one of the compartments filled with the testing liquid. The testing gas displaces the testing liquid from the compartment. By filling the compartment with testing gas and generating a positive pressure of the testing gas, a pressure gradient is established between the compartments.

The magnitude of the pressure gradient is not critical for the process. It will be chosen to be large enough to be within the measuring range of the equipment used for monitoring the pressure gradient between the compartments of the filter or for measuring testing gas flow through the membrane, respectively. On the other hand, it will be chosen small enough not to compromise mechanical stability of the membrane or the filter.

The pressure gradient between the compartments can then be monitored or the testing gas flow through the membrane can be measured using methods known in the art, for instance with commercially available leak detectors, to verify the integrity of the filter membrane. In comparison to filters having intact membranes, filters having defective membranes show a faster decrease of the pressure gradient over time between the compartments of the filter, or an increased leak rate.

In one embodiment of the process, an overpressure is applied to one compartment of the filter after the membrane has been wetted, and the increase of pressure in the other compartment over time is monitored. As an alternative, gas flow through the membrane may be measured. In another embodiment of the process, an overpressure is applied to one compartment of the filter through an inlet of the respective compartment after the membrane has been wetted, the inlet is closed and the decrease of pressure in the compartment over time is monitored.

In one embodiment of the process, the orientation of the filter during the test is such that the membrane is in a horizontal position. In another embodiment of the process, the orientation of the filter during the test is such that the membrane is in a vertical position. Although the filter can be tested regardless of its orientation, for filters comprising a bundle of hollow fiber membranes, it is preferred that the bundle of hollow fiber membranes is in vertical position during the test.

The testing liquid may be introduced into either compartment of the filter. For filters comprising membranes having a homogeneous structure, e.g., a sponge structure, choice of the compartment is not expected to have substantial impact on the test. If the filter comprises an asymmetric membrane, it is generally preferred to introduce the predefined amount of testing liquid into the compartment bordering the selective side of the membrane, i.e. the membrane surface having the smallest pores. For example, for filters comprising a bundle of asymmetric hollow fiber membranes which have the smallest pores on the inside of the fiber, it is preferred that the predefined amount of testing liquid is introduced into the compartment encompassing the lumen of the hollow fiber membranes.

The process of the present disclosure shows improved selectivity in distinguishing damaged filters from intact filters. The process thus allows for the reliable identification of defective filters, even filters which additionally comprise particulate matter in one of the compartments. For filters comprising particulate matter, the prior art integrity tests often cannot distinguish between intact and defective filters.

In particular, known processes often produce false positives. The process of the present disclosure can advantageously be used for quality management in the context of filter production processes.

It will be understood that the features mentioned above and those described hereinafter can be used not only in the combination specified but also in other combinations or on their own, without departing from the scope of the present invention.

The present invention will now be described in more detail in the examples below. It is to be understood that the examples are not intended to limit the scope of the present invention and are merely an illustration of a preferred embodiment of the invention.

EXAMPLES

FIG. 1 shows a setup 10 for testing the integrity of a filter 11. As shown in FIG. 1, the filter 11 features two fluid ports 12, 13 connected to a first compartment within the filter 11 (the "blood ports") and two fluid ports 14, 15 connected to a second compartment within the filter 11 (the "dialysis fluid ports"). A testing liquid 16 can be introduced into the first compartment of the filter 11 via the lower blood port 13. The flow F of testing fluid 16 is monitored by flowmeter 20. A testing gas 17 can be introduced into the first compartment of the filter 11 via the upper blood port 12. The pressure P1 in the first compartment is monitored by manometer 18 and the pressure P2 in the second compartment is monitored by manometer 19 which is connected to dialysis fluid port 14. Dialysis fluid port 15 is closed during the measurement. Valves 21 are present to control the fluid flow within the setup 10. Fluids are removed from the setup via drain 22.

In an exemplary procedure, both compartments of filter 11 are filled with a testing liquid 16 through port 13. A testing gas 17 is subsequently introduced into the first compartment of filter 11 through port 12 until a predetermined overpressure P1 has been reached. Ports 12 and 13 are shut off using valves 21 and the pressure P2 within the second compartment of the filter 11 is monitored by manometer 19. In an alternative embodiment, only port 12 is shut off using valve 21 and the pressure P2 within the second compartment of the filter 11 is monitored by manometer 19.

Verification of the integrity of the membrane in the filter 11 includes monitoring the pressures P1 and P2. These can be used in several alternative ways:

For instance, the pressure P1 is measured after a predetermined period of time $\Delta T$. If the pressure has dropped by a quantity $\Delta P1 < \Delta P1_{max}$ where $\Delta P1_{max}$ is a predetermined threshold value, it is considered that the membrane is intact. If $\Delta P1 > \Delta P1_{max}$ it is considered that the membrane is not intact, or that the closed system has leaks. Alternatively it is possible to check the time the pressure P1 takes to drop beyond a predetermined limit, or to check the speed of drop of pressure P1.

Alternatively, if after a predetermined time $\Delta T$ the pressure P2 has risen by a quantity $\Delta P2 < \Delta P2_{max}$ where $\Delta P2_{max}$ is a predetermined threshold value, it is considered that the membrane is intact. If $\Delta P2 > \Delta P2_{max}$ it is presumed that the membrane is not intact, or that the closed system is subject to leakage. It is also possible to verify the time required for the pressure P2 to rise beyond a predetermined limit, or to check the speed of increase of pressure P2.

If after a time $\Delta T$, both $\Delta P1 > \Delta P1_{max}$ and $\Delta P2 > \Delta P2_{max}$, it is considered that the membrane is not intact, while if only one of the measured pressure variations $\Delta P1$ and $\Delta P2$ is greater than the respective threshold value, it is considered that the membrane is intact and that there is a leak in the circuit.

It is possible to verify the time the pressure P1 takes to fall below a predetermined limit, and to verify the time pressure P2 takes to rise beyond a predetermined limit, and it can be decided that the membrane is intact if both times exceed a predetermined minimum time. It is also possible to verify whether the speeds of change of the pressures P1 and P2 both exceed a predetermined threshold speed.

Figure 2:
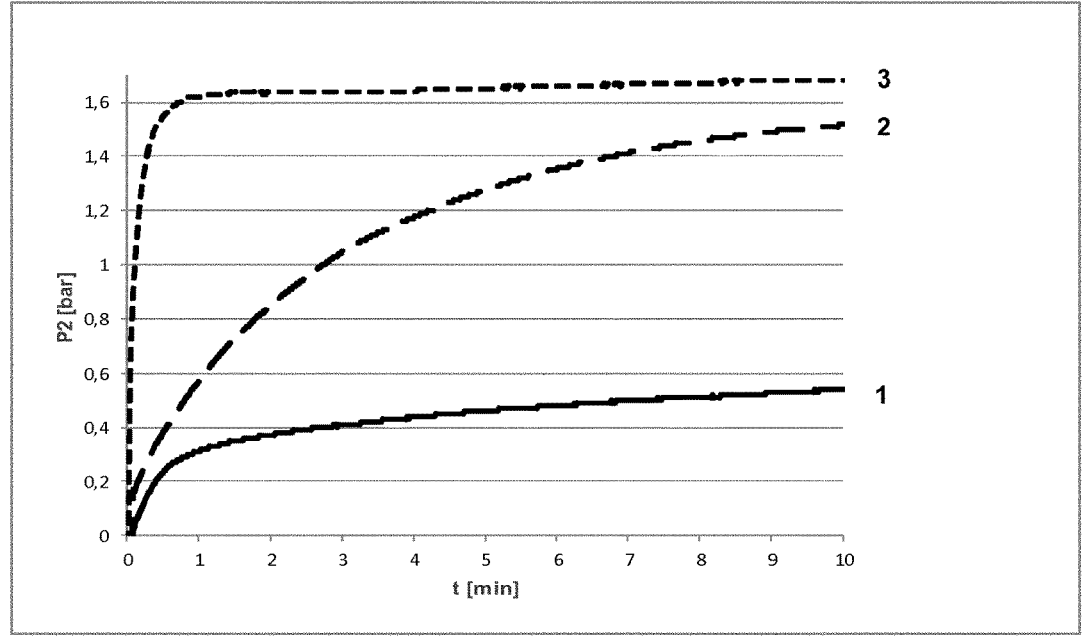
FIG. 2 shows a plot of pressure vs. time for 1: intact membrane; 2: slightly damaged membrane; 3: heavily damaged membrane.

FIG. 2 shows how the pressure P2 evolves over time for 1: a filter 11 comprising an intact membrane; 2: a filter 11 comprising a slightly damaged membrane (e.g., a membrane comprising one or more pinholes); and 3: a filter 11 comprising a severely damaged membrane (e.g., a ruptured membrane). If the membrane in the filter 11 is intact, permeation of the testing gas 17 through the membrane is controlled by diffusion. The pressure P2 in the second compartment rises slowly (curve 1). If the membrane in the filter 11 is damaged, convective transport intensifies permeation of the testing gas 17 through the membrane, accelerating the increase of pressure P2 (curve 2). In case of membrane rupture, the rise of pressure P2 is almost instantaneous (curve 3).

For filters comprising particulate matter, the prior art integrity tests often cannot distinguish between intact and defective filters. In particular, known processes often produce false positives.

Figure 3:
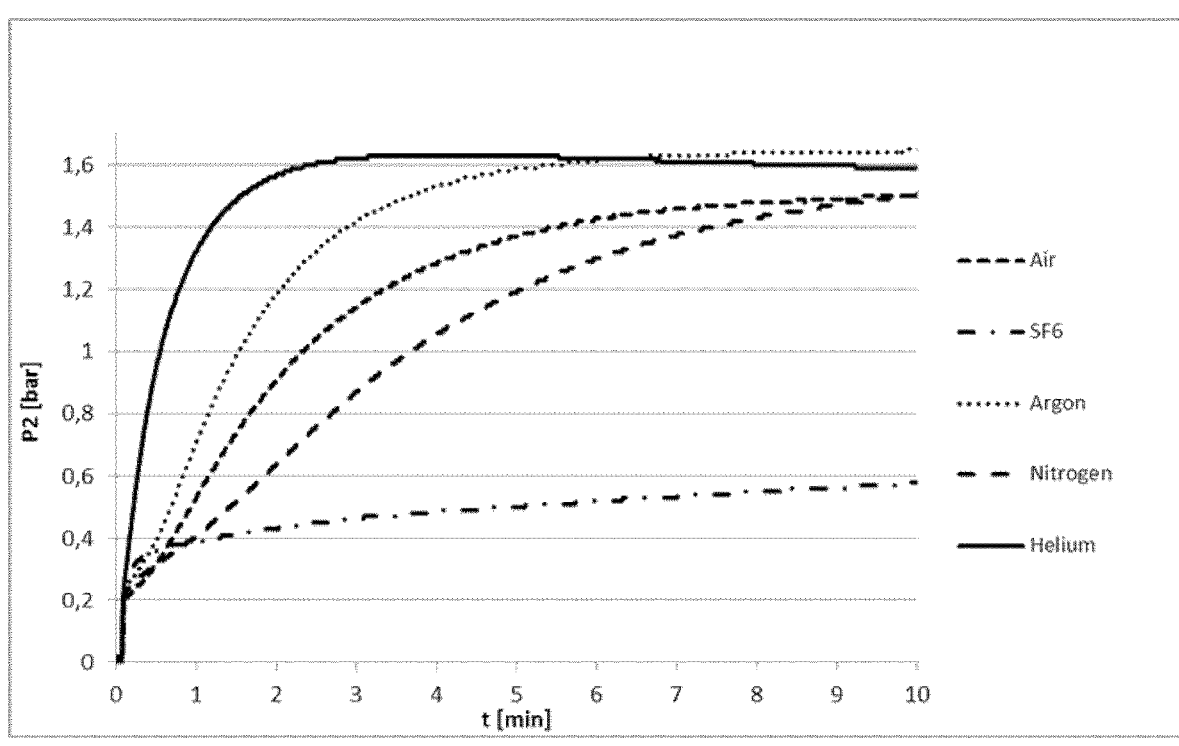
FIG. 3 shows a plot of pressure vs. time for a filter device comprising polymer beads tested with different testing gases.

FIG. 3 shows the results of integrity tests conducted on a filter device as described in EP 2 735 326 B1, Example 2. The filter device comprises a bundle of hollow fiber membranes and contains adsorbent material in the closed filtrate compartment in form of a packed beads bed surrounding the hollow fibers.

An intact filter device was used in the tests. The tests were conducted using water as testing liquid; and a different testing gas was employed in each integrity test. As can be seen in FIG. 3, only with sulfur hexafluoride ($SF_6$) as testing gas, the correct result is achieved. Nitrogen, compressed air, helium and argon yield false positive results, i.e., indicate a defective filter although the device is intact.

Figure 4:
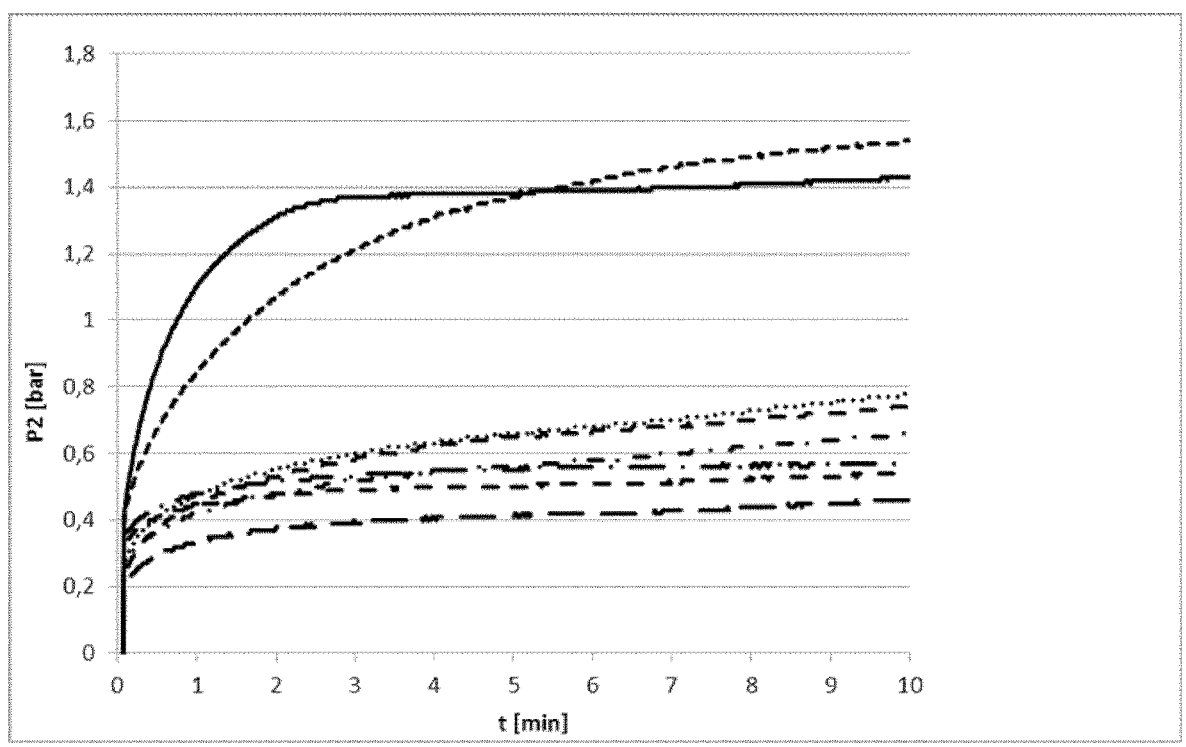
FIG. 4 shows a plot of pressure vs. time for different filter devices comprising polymer beads tested with octafluoropropane as testing gas

FIG. 4 shows the results of a series of integrity tests conducted on different filter devices comprising polymer beads (as described in EP 2 735 326 B1, Example 2). The tests were conducted using water as testing liquid; and octafluoropropane as testing gas. As can be seen from FIG. 4, the curves for the intact filter devices all fall inside a narrow window. The two defective devices are clearly distinguishable by the steeper pressure increase.

Figure 5:
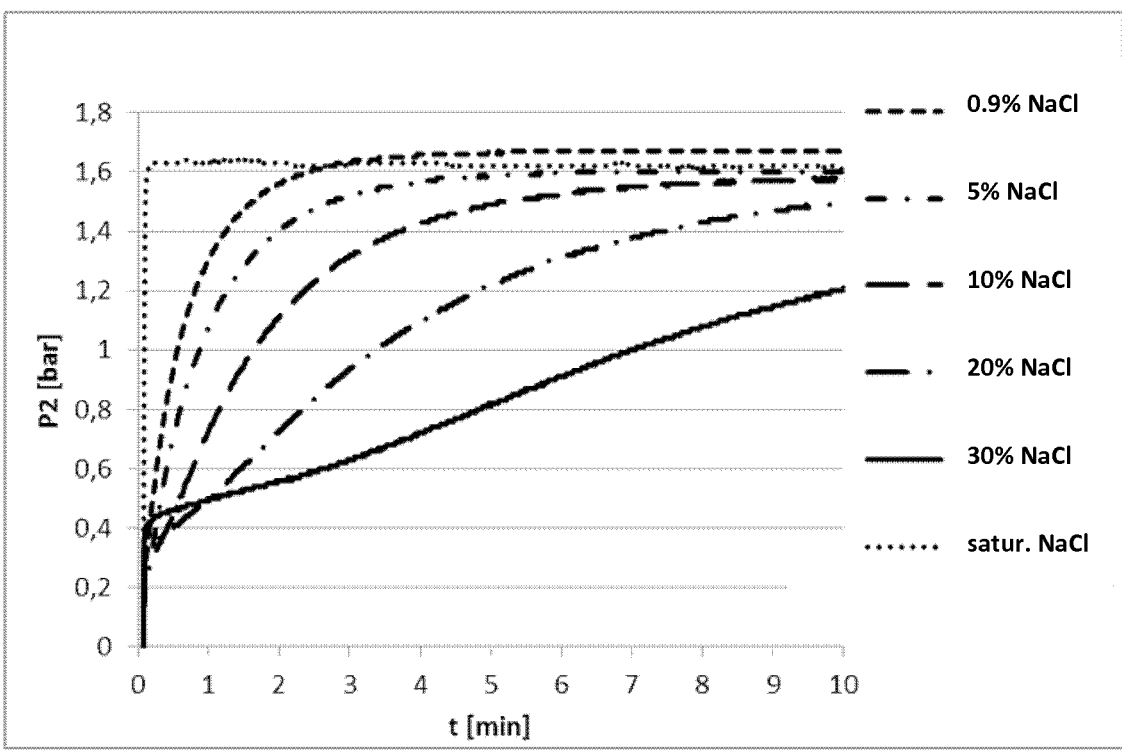
FIG. 5 shows a plot of pressure vs. time for a filter device comprising polymer beads tested with different testing liquids.

FIG. 5 shows the results of a series of integrity tests conducted on a filter device comprising polymer beads (as described in EP 2 735 326 B1, Example 2). The tests were conducted using air as testing gas; and a different testing liquid was employed in each integrity test. Aqueous solutions of sodium chloride having different salt concentrations were employed as testing liquids. Solutions containing 0.9 wt % NaCl, 5 wt % NaCl, 10 wt % NaCl, 20 wt % NaCl, and 30 wt % NaCl, respectively, as well as a saturated sodium chloride solution were used as the testing liquids.

As can be seen from FIG. 5, satisfactory results were obtained in a concentration range of from about 10 wt % to about 30 wt % NaCl. With 0.9 wt % and 5 wt % NaCl, respectively, the pressure curve is too steep to reliably distinguish between intact and defective filters. Surprisingly, saturated sodium chloride solution produced the steepest pressure curve in the test, falsely indicating a defective device.

In order to test the reliability of the integrity test, well defined holes having a diameter of 50 μm were generated in the hollow fiber membranes of a number of filter devices using a laser beam. 30 filters comprising polymer beads (22 intact filters and 8 filters comprising membranes with 50 μm holes) were tested using water as testing liquid and sulfur hexafluoride as testing gas. The results are shown in FIG. 6.

Figure 6:
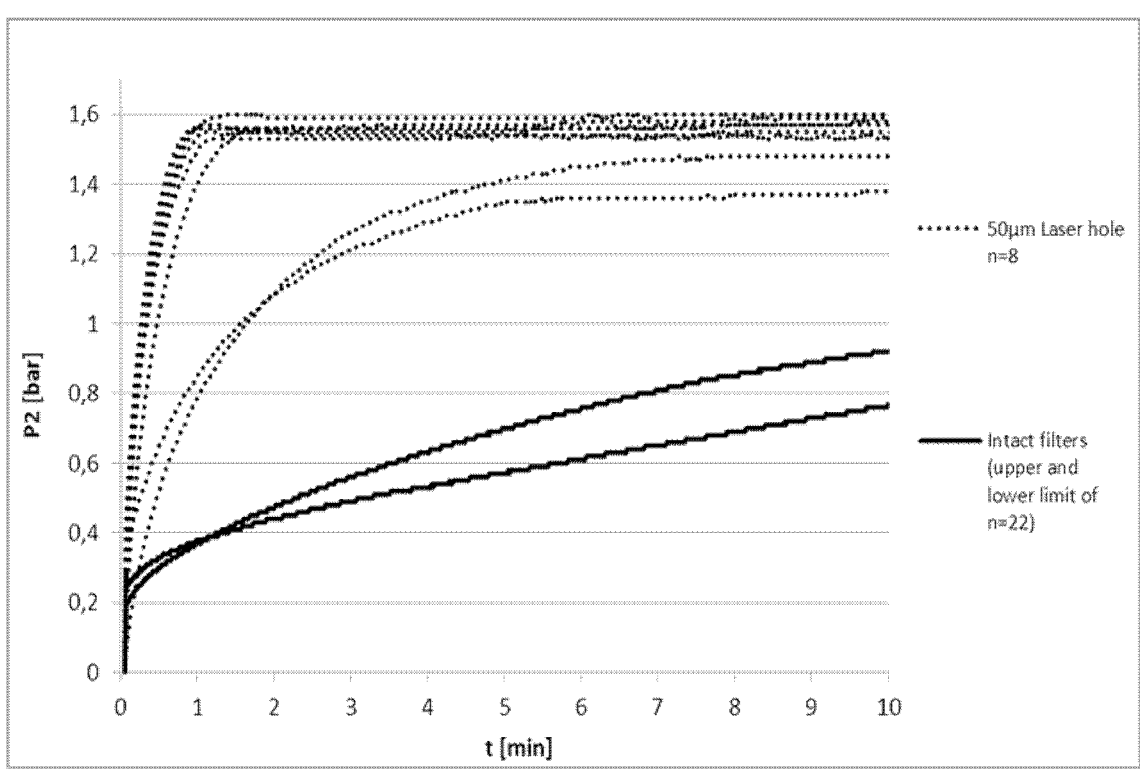
FIG. 6 shows a plot of pressure vs. time for intact filter devices comprising polymer beads and filter devices comprising polymer beads, wherein the membranes have pinholes with a diameter of 50 μm.

The solid lines in FIG. 6 represent the upper and lower limit, respectively, of the pressure curves of the intact filter devices. The curves of all 22 intact devices are within the window spanned by these solid lines. The dotted lines represent the pressure curves of the 8 filter devices comprising hollow fiber membranes having 50 μm holes. As is evident from FIG. 6, the pressure curves of the defective devices are clearly distinguished from those of the intact devices. The defective devices are reliably identified, as their pressure curves are outside the window for intact devices.

LIST OF REFERENCE SIGNS

10 Testing setup
11 filter
12 blood port
13 blood port
14 dialysate port
15 dialysate port
16 testing liquid
17 testing gas
18 manometer
19 manometer
20 flowmeter
21 valve
22 drain
F flow rate
P1 pressure
P2 pressure

The invention claimed is:

1. A process for identifying damage to a filter comprising a first compartment and a second compartment, wherein the first compartment and the second compartment are separated by a porous membrane, said process comprising the steps of:
   i) providing the filter, wherein the first compartment of the filter and the second compartment of the filter are both filled with a testing liquid;
   ii) establishing a pressure gradient between the first compartment and the second compartment by introducing a testing gas into the first compartment, thus displacing the testing liquid from the first compartment;
   iii) evaluating the filter via a) monitoring the pressure gradient established in step ii), b) measuring flow of the testing gas through the porous membrane separating the first compartment and the second compartment, or c) both;
   wherein the testing liquid is an aqueous solution of sodium chloride comprising a salt concentration in the range of from about 10 wt. % to about 20 wt. %; and
   wherein the testing gas is air.

2. The process of claim 1, wherein the first compartment of the filter comprises particulate matter selected from polymer beads and particles comprising activated carbon or the second compartment of the filter comprises particulate matter selected from polymer beads and particles comprising activated carbon.

3. The process of claim 2, wherein the first compartment of the filter comprises polymer beads or the second compartment of the filter comprises polymer beads.

4. The process of claim 1, wherein the porous membrane is a bundle of hollow fiber membranes.

5. The process of claim 2, wherein the porous membrane is a bundle of hollow fiber membranes.

6. The process of claim 3, wherein the porous membrane is a bundle of hollow fiber membranes.

7. The process of claim 1, wherein the first compartment of the filter comprises particulate matter.

8. The process of claim 1, wherein the second compartment of the filter comprises particulate matter.

9. The process of claim 1, wherein the porous membrane comprises one or more polymers selected from the group consisting of polysulfones, polyethersulfones, polyacrylonitrile, polytetrafluoroethylene, polyvinylidene fluoride, polyvinylpyrrolidone, polyetherimine ethylene vinyl acetate, and any combination thereof.

10. A process for identifying damage to a filter comprising a first compartment and a second compartment, wherein the first compartment and the second compartment are separated by a porous membrane, said process comprising the steps of:

i) providing the filter, wherein the first compartment of the filter and the second compartment of the filter are both filled with a testing liquid;

ii) establishing a pressure gradient between the first compartment and the second compartment by introducing a testing gas into the first compartment, thus displacing the testing liquid from the first compartment;

iii) evaluating the filter via a) monitoring the pressure gradient established in step ii), b) measuring flow of the testing gas through the porous membrane separating the first compartment and the second compartment, or c) both;

wherein the testing liquid is an aqueous solution of sodium chloride comprising a salt concentration of about 10 wt. %; and wherein the testing gas is air.

11. The process of claim 10, wherein the first compartment of the filter comprises particulate matter selected from polymer beads and particles comprising activated carbon or the second compartment of the filter comprises particulate matter selected from polymer beads and particles comprising activated carbon.

12. The process of claim 11, wherein the first compartment of the filter comprises polymer beads or the second compartment of the filter comprises polymer beads.

13. The process of claim 10, wherein the porous membrane is a bundle of hollow fiber membranes.

14. The process of claim 10, wherein the porous membrane comprises one or more polymers selected from the group consisting of polysulfones, polyethersulfones, polyacrylonitrile, polytetrafluoroethylene, polyvinylidene fluoride, polyvinylpyrrolidone, polyetherimine ethylene vinyl acetate, and any combination thereof.

15. A process for identifying damage to a filter comprising a first compartment and a second compartment, wherein the first compartment and the second compartment are separated by a porous membrane, said process comprising the steps of:

i) providing the filter, wherein the first compartment of the filter and the second compartment of the filter are both filled with a testing liquid;

ii) establishing a pressure gradient between the first compartment and the second compartment by introducing a testing gas into the first compartment, thus displacing the testing liquid from the first compartment;

iii) evaluating the filter via a) monitoring the pressure gradient established in step ii), b) measuring flow of the testing gas through the porous membrane separating the first compartment and the second compartment, or c) both;

wherein the testing liquid is an aqueous solution of sodium chloride comprising a salt concentration of about 20 wt. %; and wherein the testing gas is air.

16. The process of claim 15, wherein the first compartment of the filter comprises particulate matter selected from polymer beads and particles comprising activated carbon or the second compartment of the filter comprises particulate matter selected from polymer beads and particles comprising activated carbon.

17. The process of claim 16, wherein the first compartment of the filter comprises polymer beads or the second compartment of the filter comprises polymer beads.

18. The process of claim 15, wherein the porous membrane is a bundle of hollow fiber membranes.

19. The process of claim 15, wherein the porous membrane comprises one or more polymers selected from the group consisting of polysulfones, polyethersulfones, polyacrylonitrile, polytetrafluoroethylene, polyvinylidene fluoride, polyvinylpyrrolidone, polyetherimine ethylene vinyl acetate, and any combination thereof.

\* \* \* \* \*